(12) United States Patent
Ware

(10) Patent No.: US 10,327,662 B2
(45) Date of Patent: Jun. 25, 2019

(54) MENTAL DISORDER TREATMENT UTILIZING VIDEO GAME TECHNOLOGY

(71) Applicant: Crooked Tree Studios, LLC, Sunnyvale, CA (US)

(72) Inventor: Samuel Ware, Sunnyvale, CA (US)

(*) Notice: Subject to any disclaimer, the term of this patent is extended or adjusted under 35 U.S.C. 154(b) by 483 days.

(21) Appl. No.: 15/018,759

(22) Filed: Feb. 8, 2016

(65) Prior Publication Data
US 2016/0228029 A1 Aug. 11, 2016

Related U.S. Application Data

(60) Provisional application No. 62/113,974, filed on Feb. 9, 2015.

(51) Int. Cl.
| | |
|---|---|
| *A63F 9/24* | (2006.01) |
| *A61B 5/0482* | (2006.01) |
| *A61B 5/00* | (2006.01) |
| *A63F 13/46* | (2014.01) |
| *A63F 13/212* | (2014.01) |
| *A61B 5/048* | (2006.01) |

(52) U.S. Cl.
CPC .......... *A61B 5/0482* (2013.01); *A61B 5/7257* (2013.01); *A63F 13/212* (2014.09); *A63F 13/46* (2014.09); *A61B 5/048* (2013.01)

(58) Field of Classification Search
None
See application file for complete search history.

(56) References Cited

U.S. PATENT DOCUMENTS

| | | | | |
|---|---|---|---|---|
| 2006/0281543 A1* | 12/2006 | Sutton | .................. | G07F 17/32 463/29 |
| 2008/0275358 A1* | 11/2008 | Freer | ...................... | G09B 7/02 600/544 |
| 2009/0030287 A1* | 1/2009 | Pradeep | ................ | G06Q 30/02 600/300 |
| 2009/0069707 A1* | 3/2009 | Sandford | ............ | A61B 5/0482 600/545 |
| 2011/0184247 A1* | 7/2011 | Contant | ................ | G06Q 10/10 600/300 |
| 2014/0316230 A1* | 10/2014 | Denison | ............ | A61B 5/04012 600/383 |
| 2015/0351655 A1* | 12/2015 | Coleman | ............ | A61B 5/0482 600/301 |

(Continued)

OTHER PUBLICATIONS

Article titled: "Neurofeedback Training Aimed to Improve Focused Attention and Alertness in Children with ADHD: A Study of Relative Power of EEG Rhythms Using Custom-Made Software Application" by El-Baz, et al. from the Clinical EEG and Neuroscience: Official Journal of the EEG and Clinical Neuroscience Society, Jul. 2013.

(Continued)

*Primary Examiner* — Paul A D'Agostino
(74) *Attorney, Agent, or Firm* — Ferguson Case Orr Paterson LLP

(57) ABSTRACT

Methods for mental treatments, such as treatments for mental disorders, are described. Such methods can include measuring user brainwaves while the user plays a video game, such as a video game where the user is exposed to a competitive environment. The user can be rewarded within the video game based upon brainwave measurements.

21 Claims, 3 Drawing Sheets

(56) References Cited

U.S. PATENT DOCUMENTS

| | | | | |
|---|---|---|---|---|
| 2015/0365398 A1* | 12/2015 | Mattsson | ............ | G06F 21/6245 |
| | | | | 705/65 |
| 2016/0077547 A1* | 3/2016 | Aimone | ................ | G06F 3/012 |
| | | | | 345/8 |
| 2016/0170998 A1* | 6/2016 | Frank | ................ | G06F 17/30702 |
| | | | | 707/748 |

OTHER PUBLICATIONS

Article titled: "EEG Biofeedback Therapy as an Adjunct Treatment for PTSD" on the website ClinicalTrials.gov dated May 2, 2012 by Julie A. Onton.

* cited by examiner

MENTAL DISORDER TREATMENT UTILIZING VIDEO GAME TECHNOLOGY

This application claims the benefit of U.S. Provisional Patent Application No. 62/113,974 to Ware, filed on Feb. 9, 2015 and entitled "Mental Disorder Treatment Utilizing Video Game Technology", which is fully incorporated by reference herein in its entirety.

BACKGROUND OF THE INVENTION

Field of the Invention

This invention relates generally to the treatment of mental disorders using video game technology, and more particularly to the treatment of disorders through video game interaction controlled at least in part by the brain waves of the user.

Description of the Related Art

The human brain produces different types of brain waves. These waves include delta (0 Hz to 4 Hz), theta (4 Hz to 8 Hz), alpha (8 Hz to 12 Hz), beta (12 Hz to 40 Hz), and gamma (40 Hz to 100 Hz) waves. Each type of wave serves a different function, and brain disorders can result from either too few or too many of a certain type of wave, and/or can result from a ratio of the number of one wave to another that is too low or too high. Typically high frequency waves are dominant while a person is awake and low frequency waves dominate during sleep, with alpha waves serving as a link between the two that connects conscious thinking to the subconscious.

Alpha waves are known to help promote relaxation. If a person's brain produces too many alpha waves, he or she can lack focus and/or be prone to daydreaming, whereas if a person produces too few alpha waves he or she can suffer from anxiety or stress. Conversely, too many low-frequency waves can result in a lack of focus and/or disorders such as ADHD.

Neurofeedback is a type of biofeedback that measures brain waves and produces a signal that can then be utilized in a number of different ways. One such utilization of neurofeedback is to teach the self-regulation of brain function. Neurofeedback training has been utilized in the past to treat ADHD, anxiety, and similar mental disorders. For example, a 2013 study by the Department of Psychiatry & Behavioral Sciences at the University of Louisville School of Medicine subjected 18 children diagnosed with ADHD to 12 sessions of neurofeedback therapy, and found that theta/low-beta and theta/alpha ratios could be decreased significantly using such therapy. With theta being a low-frequency wave associated with daydreaming and sleep, and alpha and beta waves being higher frequency waves associated with activities while awake, the lowering of these ratios could push a brainwave pattern toward normalization from a state more commonly associated with a disorder such as ADHD. This study is described in "Neurofeedback Training Aimed to Improve Focused Attention and Alertness in Children with ADHD: A Study of Relative Power of EEG Rhythms Using Custom-Made Software Application" to Hillard et al., which is fully incorporated by reference herein in its entirety.

On the opposite end of the spectrum, too few or too many of certain types of brainwaves can cause issues such as anxiety or post-traumatic stress disorder (PTSD). For example, a study by the United States Naval Medical Center, San Diego entitled "EEG Biofeedback Therapy as an Adjunct Treatment for PTSD" showed a lack of alpha waves to be associated with PTSD. "EEG Biofeedback Therapy as an Adjunct Treatment for PTSD" is fully incorporated by reference herein in its entirety.

SUMMARY OF THE DISCLOSURE

The present disclosure relates to methods for mental treatment, such as treatment of mental disorders, including exposing a user to a video game environment and encouraging the user to control his or her brain waves in a manner so as to be successful in the video game environment.

One embodiment of a method according to the present disclosure includes exposing a user to a competitive video game environment such that the user controls a player within the environment. Brainwave measurements are obtained from the user, and the user is rewarded based on the brainwave measurements.

Another embodiment of a method according to the present disclosure includes placing a character under the control of a user, measuring the brainwaves of the user, and assigning attribute points to the character based upon the measurement results.

Yet another embodiment of method according to the present disclosure can include exposing a user to sensory stimuli within a video game, measuring the brainwaves of the user, and attributing to the user a score at least partly based upon the measuring results.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures and/or methods for carrying out the same purposes of the present disclosure. It should also be realized by those skilled in the art that such equivalent constructions and/or methods do not depart from the teachings of the disclosure as set forth in the appended claims. The novel features, which are believed to be characteristic of the disclosure, both as to its organization and method of operation, together with further features and advantages, will be better understood from the following description when considered in connection with the accompanying figures. It is to be expressly understood, however, that each of the figures is provided for the purpose of illustration and description only and is not intended as a definition of the limits of the present disclosure.

DETAILED DESCRIPTION OF THE INVENTION

The present invention relates to the use of video game technologies and scenarios, and specifically video game technologies utilizing user brain patterns, in the treatment of mental disorders such as ADHD and anxiety. In addition to or in place of traditional hand controls (e.g., "first-person shooter controls"), a user can gain an in-game benefit, or "power," through controlling his or her brain waves. This power can then be used to accomplish different in-game goals, thus encouraging the user to control his or her brain waves to gain the benefit.

It is understood that when an element is referred to as being "on" another element, it can be directly on the other element or intervening elements may also be present. Furthermore, relative terms such as "inner", "outer", "upper", "top", "above", "lower", "bottom", "beneath", "below", and similar terms, may be used herein to describe a relationship of one element to another. Terms such as "higher", "lower", "wider", "narrower", and similar terms, may be used herein to describe relative relationships. It is understood that these terms are intended to encompass all relationships which could be reasonably conveyed by their use.

Although the terms first, second, etc., may be used herein to describe various steps, elements, components, regions and/or sections, these steps, elements, components, regions, and/or sections should not be limited by these terms. These terms are only used to distinguish one step, element, component, region, or section from another. Thus, unless expressly stated otherwise, a first step, element, component, region, or section discussed below could be termed a second step, element, component, region, or section without departing from the teachings of the present invention.

Figure 1:
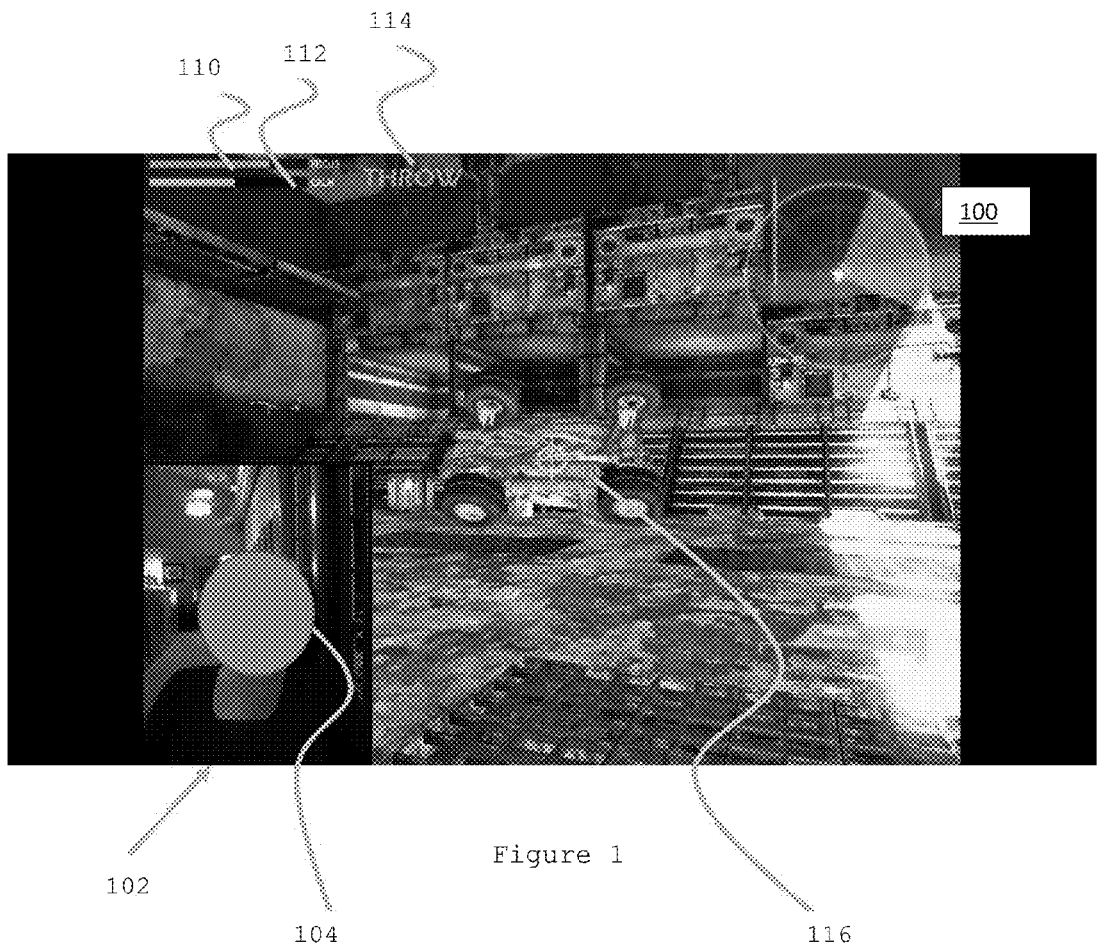
FIG. 1 illustrates a user interface according to an embodiment of the present invention.
Figure 2:
FIG. 2 illustrates a biosensor for use in conjunction with an embodiment of the present invention.

FIG. 1 shows a user interface 100, which can be used in embodiments of the present invention, with a cutout showing a user 102. The user 102 can wear an EEG biosensor 104 for reading brain waves, such as the one shown in FIG. 2 available from NeuroSky® of San Jose, Calif., USA. The software behind the interface 100 can be similar to that of various first-person shooter games in many respects, and can use a handheld controller with joystick(s) and/or buttons, or a keyboard/mouse combination, for example, to operate in various manners within the interface. Other embodiments may not use handheld or similar controllers, or may use other types of controllers in addition to or in place of those described above.

In addition to standard controls, the game can also be controlled via the biosensor 104. While the below embodiments focus on control using traditional methods in combination with biosensor control, it is understood that biosensor control may be used by itself or with any combination of other control techniques. In the specific embodiment described, two in-game attributes, FOCUS 110 and CALM 112, are controlled via brain waves read by the biosensor 104 and interpreted via the software. While this specific embodiment utilizes two brain-controllable attributes, it is understood that other embodiments can utilize fewer or more such attributes. Further, while the embodiments described herein focus upon attributes related to "focus" and "calmness", it is understood that in-game attributes can be related to any number of different mental attributes.

Brain-controllable attributes such as FOCUS 110 and CALM 112 are awarded to a user in an amount that can be controlled in any number of manners using different measurements. For example, in one embodiment, the amount of CALM 112 a user is awarded is dependent upon the prevalence of alpha waves emitted by the user's brain. Because this attribute is designed specifically to promote calmness, and because a higher number of alpha waves corresponds to calmness, this attribute can simply reward the user on a scale of 0 to 100 based on the number or percentage of alpha waves, with no detrimental effect suffered due to an excess of such waves. In other embodiments, a user can be rewarded for having fewer of a certain type of wave. In other embodiments, the score of an attribute can be based upon emission of a type or types of brainwaves within a certain optimal range, where a higher score is achieved if the number of waves is within the optimal range, and a lower score is received if the number of waves is either lower than or higher than the optimal range. The above example regarding an increase in CALM score with an increase in alpha waves can be utilized, for example, in a game having a multiplayer competitive environment. Such a scoring system—with no detrimental effect due to an excess of waves—may be appropriate in such an environment because it is highly unlikely that a user in such an embodiment will be too calm, as a multiplayer competitive environment will naturally stimulate a user's brain into activity or overactivity.

Brainwaves emitted by the user 102 can be used by the software in any number of ways. In one embodiment, data from the biosensor 104 can be provided to the software, which can take a fast Fourier transform (FFT) of blocks of the data. For example, in one embodiment, the FFT of one-second blocks of the user's alpha waves can be taken, and a score can be calculated based on this FFT. This process can then result in the user 102 receiving a CALM 112 score based on, for example, the prevalence and/or pure number of alpha brainwaves.

Attributes can also be rewarded based on a ratio of brainwaves. For example, as recognized by Hillard et al., high theta/low-beta and theta/alpha ratios are often associated with ADHD and similar issues. The FOCUS 110 score of a user can be based on a ratio of brainwaves, such as the theta/beta ratio. By controlling his or her brain to focus upon the tasks at hand, the user will produce fewer theta brainwaves and more beta brainwaves, resulting in a lower theta/beta ratio. The software can then reward FOCUS 110 points to the user based on his or her theta/beta ratio. As previously described above, the software can award FOCUS 110 points based on minimizing or maximizing a value, such as theta/beta ratio, or can award points based on achieving an optimal range. In an embodiment utilizing a multiplayer competitive environment, points can be awarded based on the minimization of theta/beta ratio. In one embodiment, the FFT of the user's theta and beta waves can be taken, and a score can be calculated based on these FFTs. This process can then result in the user 102 receiving a FOCUS 110 score based on, for example, the ratio of theta/beta waves. In another embodiment, the FFT of theta and alpha waves (or other wave(s)) can be taken and compared to determine a baseline theta/alpha (or other) ratio for the calculation of an in-game attribute, such as FOCUS 110.

A user can be rewarded by gaining FOCUS 110 or CALM 112 points accordingly. The user may then exchange an amount of the points earned for an in-game benefit such as a "power up." In another embodiment, a user is given FOCUS 110 and CALM 112 scores according to the user's current, recent, or cumulative brainwave activity. Thus the scores may reflect the user's brainwaves in real time. A threshold score may be a pre-requisite to receive an in-game benefit, the degree of an in-game benefit may be reflective of the score, or a combination of the two. In any embodiment, the FOCUS 110 and CALM 112 scores may be displayed in various manners, such as numerically and/or graphically as shown in FIG. 1 (e.g., as a pie or bar chart).

Attribute points can be used in any number of ways. In one embodiment, neurofeedback is used to award attribute points, while other tasks are performed by a user using traditional controls, such as a joystick/button configuration or a keyboard/mouse configuration. Attribute points can be used to perform a certain action and/or achieve a certain goal within the game. For example, in FIG. 1 the user 102 is using FOCUS 110 and/or CALM 112 points to perform an in-game action 114, in this case, throwing. The action performed using attribute points can be actuated using traditional controls, or in one embodiment can be activated using brainwaves. In FIG. 1, the user 102 is using attribute points gained via brainwaves to throw the truck 116 using traditional controls. In one embodiment, FOCUS 110 points can be used to perform offensive actions, while CALM 112 points can be used to perform defensive actions, such as bringing up a forcefield to protect a user's player or character. Different attribute points can be used for different types of player/character actions, and the types of player/character actions may also vary among the characters. For example, use of CALM 112 points for one character may result in a different defensive action than that of another character.

Figure 3:
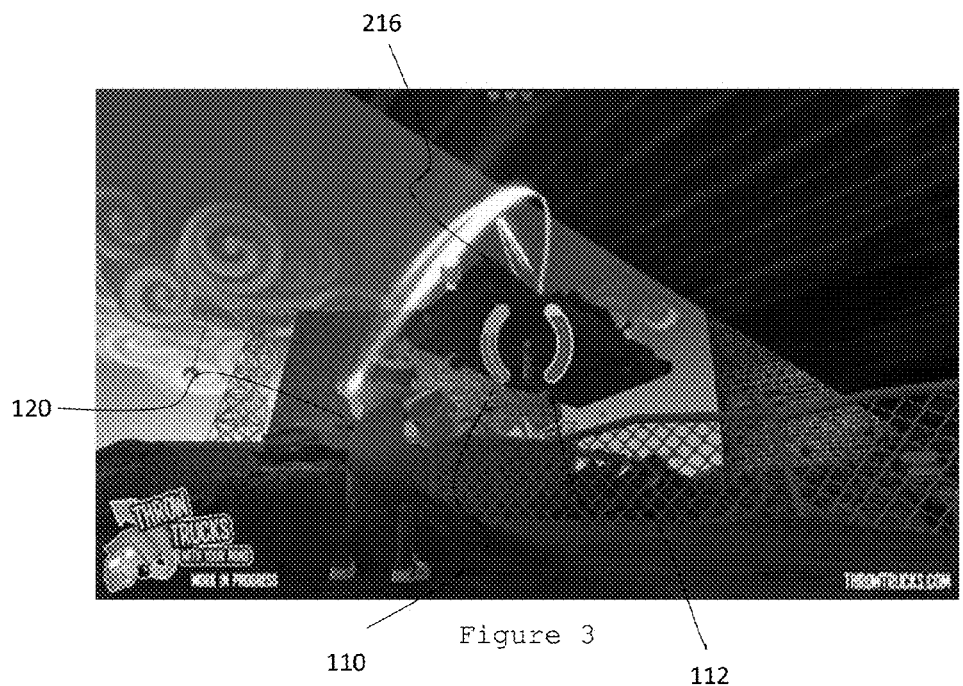
FIG. 3 illustrates a user interface according to an embodiment of the present invention.

In FIG. 3, the user's character 120 is using FOCUS 110 and/or CALM 112 points to throw a tank 216. Once the points are used, the corresponding amount of FOCUS and/or CALM 112 points are depleted on the screen. In another embodiment, points are not depleted upon use, but instead the user must have a certain threshold of points in order to perform different actions.

Figure 4:
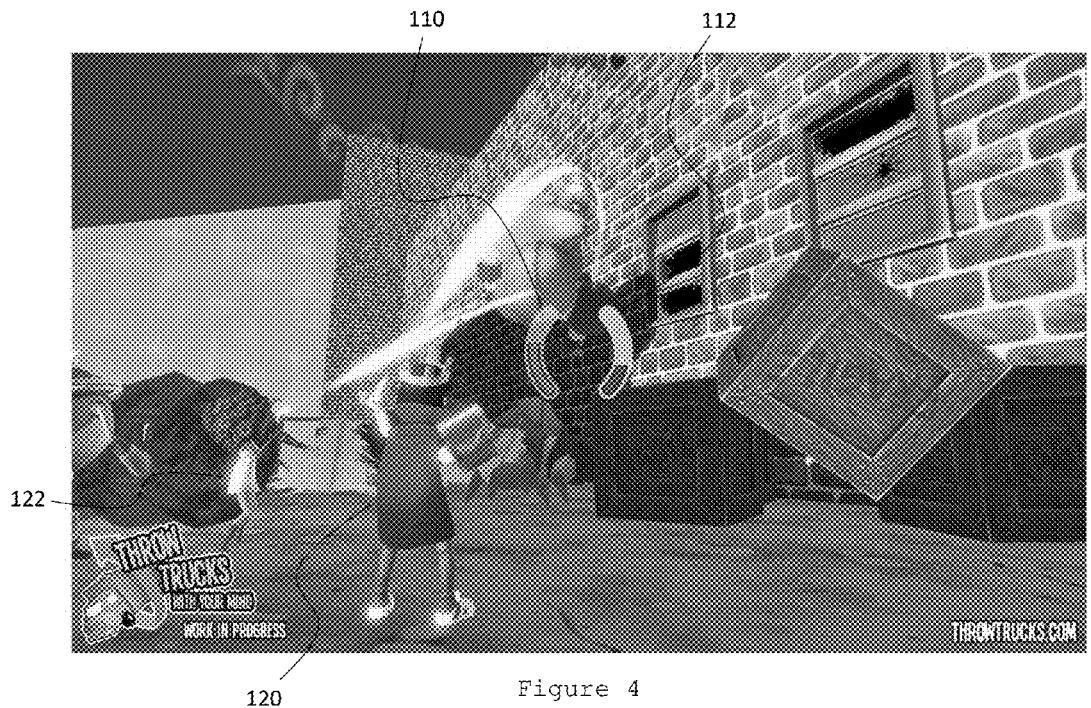
FIG. 4 illustrates a user interface according to an embodiment of the present invention.
Figure 5:
FIG. 5 illustrates a user interface according to an embodiment of the present invention.

FIG. 4 shows a multi-player mode. Here, the user's character 120 and an additional character 122 are teaming up to throw the same object, applying both of their attribute points. In multi-player mode, there may be additional one or more characters controlled by other users or the game. FIG. 5 displays the character user 120 choosing an object 118 to interact with, such as to throw it or cause it to move in a number of ways.

In embodiments of the present invention, such as the embodiment utilizing the interface 100 from FIG. 1, seemingly contradictory reward systems can be utilized in order to fine-tune the user's control of his or her brainwaves. For example, as described above, in one embodiment a user is rewarded for 1) a higher number of alpha waves, and 2) a lower theta/beta ratio. Alpha waves are typically associated with calmness; theta waves are often associated with daydreaming and sleep; and beta waves are associated with being active. Therefore, a higher number of alpha waves and a lower theta/beta ratio demonstrates calmness and focus, respectively, for which the user is rewarded by appropriate CALM 112 and FOCUS 110 scores. Thus, this embodiment rewards a user for keeping calm while also focusing. This embodiment and other embodiments like it can utilize two different reward systems which somewhat contradict each other in order to ultimately reward an optimal balance between the two, e.g., a calm, but focused and alert state of mind. Simpler embodiments, such as those for use with beginning users or those beginning treatment, may use a single attribute or attributes that are complementary to one another (e.g., low number of theta waves in combination with low theta/beta ratio). Further, while the embodiments above focus upon two-attribute systems, any number of attributes can be used.

In another embodiment, attribute points may only be rewarded when a combination of measurement thresholds are reached, in order to prevent a user from focusing upon gaining one type of attribute point and ignoring another. For example, in one embodiment utilizing FOCUS 110 based upon alpha wave prevalence and CALM 112 based upon theta/beta ratio, a user may not be awarded any points until both the number of alpha waves and the theta/beta ratio reach a predetermined threshold. The threshold may be set to a number of alpha waves lower than is required to receive CALM 112 points and a theta/beta ratio higher than is required to receive FOCUS 110 points, in which case the user could still be rewarded based upon the other attribute's score.

In one embodiment, the game may adapt to the user's FOCUS 110 and CALM 112 scores. If the scores are low for a predetermined amount of time, then the game may automatically decrease the degree of stimuli presented to the user, for example by reducing the amount or complexity of obstacles or altering background music (thus decreasing difficulty in achieving the desired neurological output). If the scores are high for a predetermined amount of time, then the game may automatically increase the degree of stimuli presented to the user (thus increasing difficulty in achieving the desired neurological output). In an additional embodiment, the game may adjust according to each individual score. For example, if the FOCUS 110 score is high for a predetermined time, then the game may adjust to present multiple stimuli simultaneously. If the CALM 112 score is high for a predetermined time, then the game may play more intense background music or add unexpected stimuli. The predetermined amount of time as well as threshold scores may be pre-set and/or adjustable by the user. The game's adaptability ensures that the user is continually challenged without being overly discouraged. Further, the amount of points awarded to a user can be adjusted based upon user capability (e.g., less points being rewarded to an experienced user for feedback that is the same as a less experienced user).

The in-game environment with which the user 102 interacts can be designed specifically to stress the user 102 in a way that is useful to the treatment of mental disorders. For example, it is well-known that a competitive video game environment can 1) cause anxiety, and/or 2) cause persons suffering from certain neurological disorders to struggle to concentrate. This can be especially true when the in-game environment is a multiplayer competitive environment, as stress levels in such environments can be increased even further. In addition to disorders such as ADHD, PTSD, and anxiety disorders, embodiments of the present invention can also be used to treat disorders such as autism spectrum disorder. Results from a non-scientific study showed that users with a history of neurofeedback therapy for attention and relaxation aspects of autistic spectrum disorder tend to excel in embodiments of the present invention utilizing a competitive video game environment, which may indicate a relationship between traditional neurofeedback techniques and those described above, and further may indicate the effectiveness of embodiments of the present invention in treating neurological disorders.

Additionally, the use of neurofeedback techniques in conjunction with traditional video game controls may achieve enhanced treatment results. This combination can force the user 102 to concentrate more than, and in a manner different from, neurofeedback-only techniques, which may utilize only brainwave measurements. Typically, anxiety would be raised with more things upon which to concentrate. Embodiments of the present invention can require both control of brainwaves and the mental processes involved in actuating traditional video game controls, thus further stressing the user.

It is further envisioned that embodiments of the present invention can be utilized in treatment of depression. Depression often manifests itself in negative thoughts spiraling out of control. A user suffering from such negative thoughts can see their FOCUS 110 and CALM 112 scores suffer, and recognize that it is negative thoughts that are causing this. The user can then learn to "block" these negative thoughts, or at the very least stop them from spiraling out of control and lessen their effect.

Regardless of any disorders or issues from which a user may suffer, poor FOCUS 110 and CALM 112 scores allow the user to recognize when an undesired response to the stimuli is occurring. Such recognition teaches the user to identify common triggers, understand the types of neurological responses caused by the triggers, and learn how to effectively counteract these responses.

Although the present invention has been described in detail with reference to certain preferred configurations thereof, other versions are possible. Therefore, the spirit and scope of the invention should not be limited to the versions described above.

I claim:

1. A method for treating mental disorders, comprising:
    applying a brainwave reader to a user such that said brainwave reader can take measurements of brainwaves produced by said user;
    exposing said user to a competitive video game environment such that said user controls a player within said competitive video game environment;
    obtaining brainwave measurements from said user while said user is exposed to said competitive video game environment; and
    rewarding said player within said competitive video game environment on a scale, the extent of said reward on said scale being based on said brainwave measurements and being higher when the user achieves more desirable brainwave measurements, said rewarding being the result of real time brainwave measurements obtained by said brainwave reader while said user is exposed to said competitive video game environment.

2. The method of claim 1, wherein said player is rewarded based on the number of alpha brainwaves emitted by said user.

3. The method of claim 1, wherein said player is rewarded based on the number of a first type of brainwave emitted compared to the total number of brainwaves emitted.

4. The method of claim 1, wherein said player is rewarded based on the ratio of a first type of brainwave emitted by said user to a second type of brainwave emitted by said user.

5. The method of claim 4, wherein said first type of brainwave is theta; and
    wherein said user is rewarded more as said ratio lowers.

6. The method of claim 5, wherein said second type of brainwave is beta.

7. The method of claim 4, wherein said first type of brainwave is gamma; and
    wherein said user is rewarded more as said ratio lowers.

8. The method of claim 1, wherein said rewarding comprises rewarding said user in at least a first category and a second category.

9. The method of claim 8, wherein said rewarding of said user in said first category comprises rewarding higher emission of brainwaves of higher than 8 Hz, and said rewarding of said second category comprises rewarding lower emission of brainwaves of lower than 8 Hz.

10. The method of claim 1, wherein said rewarding comprises rewarding said player points that can be used to perform actions within said video game environment.

11. The method of claim 1, wherein a Fourier transform is used for said measuring.

12. A method for rewarding or punishing a video game character, comprising:
    placing a character under the control of a user;
    measuring the brainwaves of said user while said character is under the control of said user; and
    assigning a scaled number of attribute points to said character;
    wherein the scaled number of attribute points assigned to said character is based upon the real time results of said measuring, wherein a higher number of attribute points is assigned to said character for more desirable real time results of said measuring and a lower number of attribute points is assigned or zero attribute points are assigned to said character for less desirable real time results of said measuring.

13. The method of claim 12, wherein the number of said attribute points is based upon the results of measuring alpha waves.

14. The method of claim 13, wherein the number of said attribute points is further based upon the results of measuring theta waves.

15. The method of claim 13, wherein the number of said attribute points is further based upon the results of measuring theta waves in proportion to the results of measuring beta waves.

16. The method of claim 12, wherein said assigning attribute points comprises rewarding said user in one or more of at least a first category and a second category.

17. The method of claim 16, wherein said rewarding of said user in said first category comprises rewarding higher emission of brainwaves of higher than 8 Hz, and said rewarding of said second category comprises rewarding lower emission of brainwaves of lower than 8 Hz.

18. The method of claim 16, wherein said rewarding of said second category is based on the ratio of a first type of brainwave emissions to a second type of brainwaves emissions.

19. The method of claim 12, wherein said attribute points are in-game benefits that can be used to perform actions within said video game environment.

20. The method of claim 12, wherein a Fourier transform is used for said measuring.

21. The method of claim 16, wherein said assigning attribute points further comprises simultaneously rewarding said user in said first category for a higher number of alpha brainwaves and rewarding said user in said second category for a lower theta/beta brainwave ratio.

* * * * *